United States Patent
Ikoma et al.

(10) Patent No.: US 12,031,014 B2
(45) Date of Patent: Jul. 9, 2024

(54) COMPOSITION, PRODUCTION METHOD FOR MOLDED OBJECT, AND MOLDED OBJECT

(71) Applicant: SEKISUI CHEMICAL CO., LTD., Osaka (JP)

(72) Inventors: Atsushi Ikoma, Ibaraki (JP); Shigeki Nomura, Osaka (JP); Rasika Dasanayake Aluthge, Ibaraki (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 1149 days.

(21) Appl. No.: 16/640,202

(22) PCT Filed: Aug. 22, 2018

(86) PCT No.: PCT/JP2018/030989
§ 371 (c)(1),
(2) Date: Feb. 19, 2020

(87) PCT Pub. No.: WO2019/039509
PCT Pub. Date: Feb. 28, 2019

(65) Prior Publication Data
US 2020/0181366 A1 Jun. 11, 2020

(30) Foreign Application Priority Data

Aug. 22, 2017 (JP) .................. 2017-159394
Sep. 26, 2017 (JP) .................. 2017-184667

(51) Int. Cl.
| C08K 5/56 | (2006.01) |
| B27N 3/00 | (2006.01) |
| B32B 3/00 | (2006.01) |
| C07F 3/06 | (2006.01) |
| C08K 5/09 | (2006.01) |
| C08K 5/10 | (2006.01) |

(52) U.S. Cl.
CPC .................. *C08K 5/56* (2013.01); *B27N 3/00* (2013.01); *B32B 3/00* (2013.01); *C07F 3/06* (2013.01); *C08K 5/09* (2013.01); *C08K 5/10* (2013.01)

(58) Field of Classification Search
None
See application file for complete search history.

(56) References Cited

U.S. PATENT DOCUMENTS

| 2006/0185388 A1 | 8/2006 | Muller et al. |
| 2010/0226991 A1 | 9/2010 | Horcajada-Cortes et al. |
| 2010/0273642 A1 | 10/2010 | Chang et al. |
| 2016/0159822 A1 | 6/2016 | Tan et al. |
| 2016/0361702 A1 | 12/2016 | Cohen et al. |
| 2017/0031473 A1 | 2/2017 | Fujiki et al. |

FOREIGN PATENT DOCUMENTS

| CN | 105418923 | 3/2016 |
| JP | 2007-518707 | 7/2007 |
| JP | 2008-531939 | 8/2008 |
| JP | 2010-527890 | 8/2010 |
| JP | 2011-501739 | 1/2011 |
| JP | 2011-517309 | 6/2011 |
| JP | 2016-108342 | 6/2016 |
| JP | 2017-033214 | 2/2017 |
| WO | 2006/089908 | 8/2006 |
| WO | 2008/143385 | 11/2008 |
| WO | 2016/204301 | 12/2016 |

OTHER PUBLICATIONS

Z. Zhang et al., "polyMOFs: A Class of Interconvertible Polymer-Metal-Organic-Framework Hybrid Materials" (Angew. Chem. Int. Ed.; 54, 2015, pp. 6152-6157).
L. Huang et al., "Synthesis, Morphology Control, and Properties of Porous Metal-Organic Coordination Polymers" (Microporous and Mesoporous Materials; 58, 2003, pp. 105-114).
Su, Jian et al., "Structural Induction Effect of a Zwitterion Pyridiniumolate for Metal-Organic Frameworks," Inorganic Chemistry, 54 (13), 2015, pp. 6169-6175.
International Search Report issued in International Patent Application No. PCT/JP2018/030989, dated Oct. 30, 2018; and English-language translation thereof.
Japanese Office Action in corresponding Japanese App. No. 2019-537654, dated Aug. 30, 2022, along with English translation.
Chinese Office Action in corresponding Chinese App. No. 201880059672.6, dated Mar. 14, 2022, along with English translation.
Ning et al., "Carbon-based materials with tunable morphology confined Ni (0) and Ni—$N_x$ active sites: Highly efficient selective hydrogenation catalysts," Carbon, 154, 2019, pp. 48-57.

*Primary Examiner* — Chinessa T. Golden
(74) *Attorney, Agent, or Firm* — GREENBLUM & BERNSTEIN, P.L.C.

(57) ABSTRACT

A composition comprising: a substance (A) comprising at least one metal atom selected from the group consisting of zinc, cobalt, niobium, zirconium, cadmium, copper, nickel, chromium, vanadium, titanium, molybdenum, magnesium, iron and aluminum, with the proviso that a metal organic framework is excluded; an organic substance (B) having at least two metal coordination sites capable of being coordinated to the metal atom to form a crystal, wherein the metal coordination sites are of at least one type selected from the group consisting of a carboxy group and a metal organic framework; and a coordination promoter (C) that undergoes a reaction or a phase transition upon stimulation to promote the coordination of the metal coordination sites of the organic substance (B) to the metal atom of the substance (A).

23 Claims, No Drawings

COMPOSITION, PRODUCTION METHOD FOR MOLDED OBJECT, AND MOLDED OBJECT

TECHNICAL FIELD

The present invention relates to a composition, a method for producing a shaped product, and a shaped product.

Priorities are claimed on Japanese Patent Application No. 2017-159394, filed Aug. 22, 2017, and Japanese Patent Application No. 2017-184667, filed Sep. 26, 2017, the contents of which are incorporated herein by reference.

BACKGROUND ART

A metal organic framework (hereinafter also referred to as "MOF") is a crystalline porous substance formed through coordination bond between and self-assembly of metal ions and organic cross-linking ligands (polydentate ligands), and has uniform micropores and a high specific surface area. In recent years, various applications of MOFs have been studied. Examples of such applications include gas separation, gas storage, sensors, DDS (drug delivery systems), electromagnetic shielding, selective catalysts, dielectrics, precursors of porous simple metals, precursors of porous metal oxides, and the like.

As the organic cross-linking ligand, a compound having a rigid molecular structure such as 1,4-benzenedicarboxylic acid is usually used. It has also been proposed to use polymers as the organic cross-linking ligand (see Non-Patent Document 1 and Patent Document 1).

The combination of the metal ions and the organic cross-linking ligands affects how easily a coordination bond is formed. In the case where a coordination bond is not easily formed, a solvothermal method (also referred to "hydrothermal method") is widely used for the synthesis of MOF.

However, the solvothermal method requires a high-pressure environment a sealed space, so that the productivity of MOF is low. Further, MOF can be obtained only as microcrystalline particles of a micro size or smaller, or as a thin layer film formed by precipitation and condensation, and hence the shapability is poor.

A method is proposed, which adds triethylamine during the synthesis of MOF from $Zn(NO_3)_2$ and 1,4-benzenedicarboxylic acid (Non-Patent Document 2). The addition of triethylamine allows the reaction to proceed in an atmospheric pressure environment, increasing the productivity MOF.

However, in this method, the reaction proceeds rapidly, so that it is difficult to control the rate of crystal formation. As a result, MOF can be obtained only as microcrystalline particles of a micro size or smaller, and the shapability of the MOF is poor.

When the MOF in the form of microcrystalline particles is blended with a hinder to obtain a shaped product containing the MOF, various problems arise. For example, the MOF is broken during the blending or shaping, the MOF and the binder cannot be uniformly blended, the blended MOF is easily released from the resin, and the porous surface is covered with the resin, so that the functions stemming from the porousness of the MOF cannot be exploited.

DESCRIPTION OF PRIOR ART

Patent Document

Patent Document 1: US Patent Application Publication No. 2016/0361702

Non-Patent Document

Non-Patent Document 1: Angew. Chem. Int. Ed. 2015, 54, 6152-6157
Non-Patent Document 2: Microporous and Mesoporous Materials 58 (2003) 105-114

DISCLOSURE OF INVENTION

Problems to be Solved by the Invention

The object of the present invention is to provide: a composition capable of generating MOF even without a high-pressure environment such as required in the solvothermal method, and capable of being stored as a shapable material; a method for producing a shaped product using the composition; and a shaped product.

Means to Solve the Problems

The embodiments of the present invention are as follows.

[1] A composition including: a substance (A) including at least one metal atom selected from the group consisting of zinc, cobalt, niobium, zirconium, cadmium, copper, nickel, chromium, vanadium, titanium, molybdenum, magnesium, iron and aluminum, with the proviso that a metal organic framework is excluded an organic substance (B) having at least two metal coordination sites capable of coordinating to the metal atom to form a crystal, wherein the metal coordination sites are of at least one type selected from the group consisting of a carboxy group and a metal organic framework; and a coordination promoter (C) that undergoes a reaction or a phase transition upon stimulation to promote the coordination of the metal coordination sites of the organic substance (B) to the metal atom of the substance (A).

[2] The composition according to [1], wherein the stimulus is at least one selected from the group consisting of heat, light, water, and oxygen.

[3] The composition according to [1] or [2], wherein the coordination promoter (C) is solid at 25° C. and has a pKa of 1 to 20.

[4] The composition according to any one of [1] to [3], wherein the coordination promoter (C) is at least one selected from the group consisting of an amine-borane complex, dicyandiamide, a hydrazide, an imine, oxazolidine, pyridine, a tertiary amine that is crystalline at room temperature, a ketoprofenamine salt, calcium oxide, and iron.

[5] The composition according to any one of [1] to [4], wherein a crystal formed by coordination of the metal coordination sites of the organic substance (B) to the metal atom of the substance (A) is present in an amount of 99% by mass or less.

[6] The composition according to any one of [1] to [4], wherein a crystal in which the metal coordination sites of the organic substance (B) are coordinated to the metal atom of the substance (A) is present in an amount of 50% by mass or less.

[7] The composition according to any one of [1] to [4], wherein a crystal in which the metal coordination sites of the organic substance (B) are coordinated to the metal atom of the substance (A) is present in an amount of 10% by mass or less.

[8] The composition according to any one of [1] to [4], wherein a crystal in which the metal coordination sites of the organic substance (B) are coordinated to the metal atom of the substance (A) is present in an amount of 1% by mass or less.

[9] The composition according to any one of [1] to [8], wherein the organic substance (B) has an aromatic ring having one or more of the metal coordination sites.

[10] The composition according to any one of [1] to [8], wherein the organic substance (B) has an aromatic ring having two or more of the metal coordination sites.

[11] The composition according to [10], wherein the metal coordination sites are carboxy groups.

[12] The composition according to any one of [1] to [11], wherein the organic substance (B) has a molecular weight of 100 or more.

[13] The compo according to any one of [1] to [12], wherein the organic substance (B) is a polymer having a main chain and a pendant structure bonded to the main chain, wherein the pendant structure includes the metal coordination sites.

[14] The composition according to [13], wherein the main chain includes at least ne structure selected from the group consisting of a polyether structure, a polyolefin structure, a polyester structure, a polythiol structure, and a polyamide structure.

[15] The composition according to any one of [1] to [14], wherein the substance (A) is at least one substance selected from the group consisting of a simple metal and a metal compound having a valence of 1 to 5.

[16] The composition according to any one of [1] to [15], which further includes at least one organic substance (D) selected from the group consisting of a polymer having a constitutional unit having one metal coordination site capable of being coordinated to the metal atom to form a crystal, a monomer having one metal coordination site defined above, and an organic substance having no metal coordination site defined above.

[17] The composition according to any one of [1] to [ ], which further includes a liquid medium (E).

[18] The composition according to [17], wherein the amount of the liquid medium (E) is 99% by mass or less.

[19] The composition according to [17] or [18], which further includes a resin (F) capable of holding the liquid medium (E).

[20] A method for producing a shaped product, comprising:
  shaping the composition according to any one of [1] to [19] to obtain shaped product (Y); and
  applying a stimulus to the shaped product (Y) to form a crystal in which the metal coordination sites of the organic substance (B) are coordinated to the metal atoms of the substance (A) to thereby obtain a shaped product (Z) containing the crystal.

[21] The method according to [20], wherein the stimulus is at least one selected from the group consisting of heat, light, water, and oxygen.

[22] The method according to [20] or [21], wherein an amount of the crystal in the shaped product (Y) is 99% by mass or less.

[23] The method according to any one [20] to [22], wherein the shaped product (Z) is obtained such that the amount of the crystal in the shaped product (Z) is 0.1% by mass or more.

[24] The method according to any one of [1] to [19], wherein the stimulus is applied to the composition of any one of [1] to [19] while shaping the composition, so as to form the crystal in which the metal coordination sites of the organic substance (B) are coordinated to the metal atom of the substance (A) to thereby obtain the shaped product (Z) containing the crystal.

[25] A shaped product including: a crystal in which metal coordination sites of an organic substance (B) are coordinated to a metal atom of substance (A), wherein the organic substance (B) has at least two metal coordination sites which are of at least one type selected from the group consisting of a carboxy group and a metal organic framework, and the substance (A) includes at least one metal atom selected from the group consisting of zinc, cobalt, niobium, zirconium, cadmium, copper, nickel, chromium, vanadium, titanium, molybdenum, magnesium, iron and aluminum, with the proviso that a metal organic framework is excluded; and a coordination promoter (C) that undergoes a reaction or a phase transition upon stimulation to promote the coordination of the metal coordination sites of the organic substance (B) to the metal atom of the substance (A).

Effect of the Invention

The present invention can provide: a composition capable of generating MOF even without a high-pressure environment such required in the solvothermal method, and capable of being stored as a shapable material; a method for producing a shaped product using the composition; and a shaped product.

DESCRIPTION OF THE EMBODIMENTS

Composition

The first aspect of the present invention relates to a composition containing a substance (A), an organic substance (B), and a coordination promoter (C) (hereinafter, also referred to as "composition I").

The substance (A) includes at least one metal atom selected from the group consisting of zinc, cobalt, niobium, zirconium, cadmium, copper, nickel, chromium, vanadium, titanium, molybdenum, magnesium, iron and aluminum, with the proviso that an metal organic framework is excluded.

The organic substance (B) has at least two metal coordination sites capable of being coordinated to the metal atom to form a crystal. The metal coordination sites of the organic substance (B) are of at least one type selected from the group consisting of a carboxy group and a metal organic framework.

The coordination promoter (C) is a substance that undergoes a reaction or a phase transition upon stimulation to promote the coordination of the metal coordination sites of the organic substance (B) to the metal atom of the substance (A).

The composition I may further include one or more of an organic substance (D), a liquid medium (E), a resin (F), and a component (G) other than mentioned above, if necessary.

The organic substance (D) is at least one organic substance selected from the group consisting of a polymer having a constitutional unit having one metal coordination site capable of being coordinated to the metal atom of the substance (A) to form a crystal, a monomer having one metal coordination site defined above, and an organic substance having no metal coordination site defined above, with the proviso that the organic substance (B) and the resin (F) described later are excluded.

The resin (F) is a resin capable of holding the liquid medium (E). In the present specification and claims, "to"

indicating a numerical range means that the numerical values described before and after "to" are included as the lower limit and the upper limit of the range.

<Substance (A)>

The substance (A) is at least one metal atom (hereinafter, also referred to as "metal atom α") selected from the group consisting of zinc, cobalt, niobium, zirconium, cadmium, copper, nickel, chromium, vanadium, titanium, molybdenum, magnesium, iron, and aluminum. The metal atom α contained in the substance (A) may be of one type or two or more types.

As the metal atom α, those exhibiting a valence of 1 to 5 when ionized are preferable, and those exhibiting a valence of 1 to 4 when ionized are more preferable.

The substance simple metal or a metal compound. The metal in each of the simple metal and the metal compound is at least one metal selected from the group consisting of zinc, cobalt, niobium, zirconium, cadmium, copper, nickel, chromium, vanadium, titanium, molybdenum, magnesium, and aluminum. Examples of the metal compound include metal salts such as nitrates, carbonates, halide salts and sulfates; metal oxides; and metal hydroxides. The metal salts may be hydrates.

Specific examples of the substance (A) include zinc, zirconium, chromium aluminum, $Zn(NO_3)_2 \cdot 6H_2O$, and $Al(NO_3)_2 \cdot 9H_2O$.

The substance (A) is preferably at least one selected from the group consisting of a simple metal and a metal compound having a valence of 1 to 5 in terms of stability in air environment. The metal in these simple metals and metal compounds is preferably at least one selected from the group consisting of zinc, zirconium, and chromium.

The substance (A) contained in the composition I may be of one type or two or more types.

<Organic Substance (B)>

The organic substance (B) has at last two metal coordination sites (hereinafter, also referred to as metal coordination sites β) which are of at least one type selected from the group consisting of a carboxy group and a MOF moiety. When two or more metal coordination sites β a coordinated to the metal atom α, a crystal (MOF) is generated. The two or more metal coordination sites β of the organic substance (B) may be the same or different.

The MOF moiety in the metal coordination sites β is not particularly limited, and may be a known MOF. Known MOFs include, but are not limited to, MOFs having a plurality of metals, metal oxides, metal clusters, or metal oxide cluster structural units. The metals can be selected from transition metals and beryllium. More specific examples include Zn, Cd, Hg, Be, Cu, Zr, Cr, Mo, V, Ti, Co, and the like.

A plurality of metal structural units can be linked by an organic cross-linking ligand to form a porous structure. The organic cross-linking ligand that links adjacent metal structural units is an organic compound having two or more metal coordination sites capable of being coordinated to a metal, the examples of which include 1,3,5-tris(4-carboxyphenyl) benzene (BTB), 1,4-benzenedicarboxylic acid (BDC), 2,5-dihydroxy-1,4-benzenedicarboxylic acid (DOBDC), cyclobutyl-1,4-benzenedicarboxylic acid (CB BDC), 2-amino-1,4-benzenedicarboxylic acid (H2N BDC), tetrahydropyrene-2,7-dicarboxylic acid (HPDC), terphenyldicarboxylic acid (TPDC), 2,6-naphthalenedicarboxylic acid 2,6-NDC), pyrene-2,7-dicarboxylic acid (PDC), biphenyldicarboxylic acid (BPDC) any dicarboxylic acids with a phenyl compound, 3,3', 5,5'-biphenyltetracarboxylic acid, imidazole, benzimidazole, 2-nitroimidazole, cyclobenzimidazole, imidazole-2-carboxaldehyde, 4-cyanoimidazole, 6-methylbenzimidazole, 6-bromobenzimidazole and the like.

Specific examples of the MOF include MOF-177 having a structure represented by $Zn_4O(1,3,5\text{-benzenetribenzoate})_2$; MOF-5 (also known as IRMOF-1) having a structure represented by $Zn_4O(1,4\text{-benzenedicarboxylate})_3$; MOF-74 (Mg) having a structure represented by $Mg_2(2,5\text{-dihydroxy-1,4-benzenedicarboxylate})$; MOF-74(Zn) represented by $Zr_2(2,5\text{-dihydroxy-1,4-benzenedicarboxylate})$; MOF-505 having a structure represented by $Cu_2(3,3',5,5'\text{-biphenyltetracarboxylate})$; IRMOF-6 having a structure represented by $Zn_4O(\text{cyclobutyl } 1,4\text{-benzenedicarboxylate})$; IRMOF-3 having a structure represented by $Zn_4O(2\text{-amino } 1,4\text{-benzenedicarboxylate})_3$; IRMOF-11 having a structure represented by $Zn_4O(\text{terphenyl dicarboxylate})_3$ or $Zn_4O(\text{tetrahydropyrene } 2,7\text{-dicarboxylate})_3$; IRMOF-8 having a structure represented by $Zn_4O(2,6\text{-naphthalenedicarboxylate})_3$; ZIF-68 having a structure represented by Zn(benzimidazolate)(2-nitroimidazolate); ZIF-69 having a structure represented by Zn(cyclobenzimidazolate)(2-nitroimidazolate); ZIF-7 having a structure represented by $Zn(\text{benzimidazolate})_2$; ZIF-9 having a structure represented by $Co(\text{benimidazolate})_2$; ZIF-11 having a structure epresented by $Zn_2(\text{benzimidazolate})$; ZIF-90 having a structure represented by $Zn(\text{imidazolate-2-carboxaldehyde})_2$; ZIF-82 having a structure represented by Zn(4-cyanoimidazolate)(2-nitroimidazolate); ZIF-70 having a structure represented by Zn(imidazolate)(2-nitroimidazolate); having a structure represented by Zn(6-methylbenzimidazolate)(2-nitroimidazolate); and ZIF-81 represented by Zn(6-bromobenzimidazolate)(2-nitroimidazolate).

Example of the preferred combination of the metal atom α and the metal coordination site β include a combination of Zn as the metal atom α and either a carboxy group and a MOF moiety as the metal coordination site β, a combination of Al as the metal atom α and either a carboxy group or an MOE moiety as the metal coordination site β, and a combination of Zr as the metal atom α and either a carboxy group and an MOF moiety as the metal coordination site β.

The organic substance (B) preferably has an aromatic ring having one or more metal coordination sites β in terms of coordination ability and rigidity, and more preferably has an aromatic ring having two or more metal coordination sites β. When the aromatic ring has one metal coordination site β, the organic substance (B) has two or more such aromatic rings. When the aromatic ring has two or more metal coordination sites β, each organic substance (B) may have one or two or more such aromatic rings. The rigidity of the obtained crystal increases as the number of metal coordination sites β increases. However, too many metal coordination sites β may result in brittle crystal. In such a case, the number of metal coordination sites β may be three or less. That is, from the viewpoint of balancing the rigidity and brittleness of the crystal, the number of metal coordination site β can be appropriately adjusted within the range of 1 to 3.

The metal coordination site β of the aromatic ring is preferably a carboxy group in terms of coordination ability. Examples of the aromatic ring include a dicarboxybenzene ring and a tricarboxybenzene ring.

A carboxy group not bonded to an aromatic ring shows weak metal coordination. Further, a carboxy group not bonded to an aromatic ring (for example, a carboxy group of polyacrylic acid) does not usually form a crystal even when coordinated to the metal atom α. A carboxy group that does not form a crystal does not fall within the definition of the metal coordination site β.

The organic substance (B) may be a polymer or a monomer (non-polymer).

Examples of the polymer include a polymer having a main chain and a pendant structure bonded to the main chain, wherein the pendant structure includes the metal coordination sites β; and a polymer that has a main chain having the metal coordination sites β at its ends. Of these, preferable in terms of shapability is a polymer having a main chain and a pendant structure bonded to the main chain, wherein the pendant structure includes the metal coordination sites β.

The structure of the main chain is not particularly limited, and examples thereof include a polyether structure, a polyolefin structure, a polyester structure, a polythiol structure, and a polyamide structure. The main chain may have any one of these structures, or may have two or more of the structures.

When the polymer has an aromatic ring having one or more metal coordination sites β defined above, the aromatic ring may be present in the main chain or may be present in the pendant structure.

The polymer containing the metal coordination site β in the pendant structure can be obtained, for example, by a method using a monomer having the metal coordination site β as a monomer forming the polymer. Examples of the monomer containing the metal coordination site β include a non-polymer described below.

A polymer having a MOF moiety in the pendant structure can also be obtained by a polymerization reaction between the pendant structure of the polymer and a MOF.

Specific examples of the organic substance (B) which is a polymer include polyethers having structural units represented by formula (b1) shown below, polyethylenes, and polyamides.

The number of the metal coordination sites β included in the polymer is, for example, preferably 2 or more, and more preferably 2 to 4, per structural unit constituting the polymer.

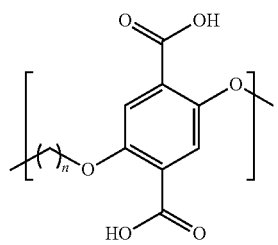
(b1)

In the formula (b1), n is an integer of 5 to 8.

Specific examples of the non-polymer as the organic substance (B) include 1,3,5-tris(4-carboxyphenyl)benzene, 1,3,5-benzenetricarboxylic acid, 1,4-benzenedicarboxylic acid, 2,5-dihydroxy-1,4-benzenedicarboxylic acid, cyclobutyl-1,4-benzenedicarboxylic acid, 2-amino-1,4-benzenedicarboxylic acid, tetrahydropyrene-2,7-dicarboxylic acid, terphenyldicarboxylic acid, 2,6-naphthalenedicarboxylic acid, pyrene-2,7-dicarboxylic acid, biphenyldicarboxylic acid, 3,3', 5,5'-biphenyltetracarboxylic acid and the like.

The number of metal coordination site β included in the non-polymer may be, for example, 2 to 4.

The molecular weight of the organic substance (B) can be appropriately selected in consideration of shapability and the like.

The molecular weight of the organic substance (B) is preferably 100 or more from the viewpoint of shapability.

When the organic substance (B) is not a non-polymer, the molecular weight of the organic substance (B) is more preferably from 100 to 10,000, even more preferably from 100 to 1,000.

When the organic substance (B) is a polymer, the molecular weight of the organic substance (B) is more preferably 100 to 100,000, even more preferably 100 to 10,000.

The molecular weight of the polymer is a weight average molecular weight measured by GPC (gel permeation chromatography).

The organic substance contained in the composition I may be of one type or two or more types.

The organic substance (B) preferably contains at least a polymer from the viewpoint that the excellent shapability of the composition I is further enhanced. The polymer and the non-polymer may be used in combination.

The amount of the polymer in the organic substance (B) is preferably 10 to 100% by mass, and more preferably 50 to 100% by mass, based on the total mass of the organic substance (B).

<Coordination Promoter (C)>

The coordination promoter (C) undergoes a reaction or a phase transition upon stimulation. Further, after the reaction or the phase transition the promotion of coordination of the metal coordination sites β to the metal atom α is enabled.

The reaction of the coordination promoter (C) includes a reaction between molecules of the coordination promoter (C) and a reaction with another substance. The phase transition is typically a change from a solid to a liquid.

The stimulus for causing the coordination promoter (C) to undergo a reaction or a phase transition is preferably at least one selected from the group consisting of heat, light, water and oxygen from the viewpoint of productivity. The stimulus are described later in detail. The stimulus for causing the coordination promoter (C) to undergo a reaction or a phase transition may be of one type or two or more types.

Examples of the reaction or phase transition by heat include decomposition and dissolution of the molecules of the coordination promoter (C). Examples of the reactions or phase transition induced by light include decomposition of the molecules of the coordination promoter (C). Examples of the reaction or phase transition caused by water include hydration and oxidation. Examples of the reaction or phase transition caused by oxygen include oxidation.

Examples of the coordination promoter (C) include an amine-borane complex, dicyandiamide, a hydrazide, an imine, oxazolidine, pyridine, a tertiary amine, a ketoprofenamine salt, calcium oxide, iron and the like.

Among these, the coordination promoter (C) is preferably at least one selected from the group consisting of an amine-borane complex, dicyandiamide, a hydrazide, an imine, oxazolidine, pyridine, a tertiary amine that is in crystalline at room temperature, a ketoprofenamine salt, calcium oxide, and iron, and more preferably at least one selected from the group consisting of dicyandiamide, a hydrazide, an imine, and a ketoprofenamine salt, because such a coordination promoter (C) allows for relatively low reaction temperature. Specific examples of the amine constituting the amine-borane complex include triethylamine. In the present specification, the "room temperature" means a temperature within 15±15° C. Specific examples of the tertiary amine that is crystalline at room temperature include dimethylpalmitylamine, dimethylstearylamine and the like. Specific examples of the ketoprofen amine salt include ketoprofen triethylamine salt and the like.

The coordination promoter (C) is preferably a solid at 25° C. for suppressing the promotion of the coordination of the metal coordination sites β to the metal atom α during storage of the composition.

The coordination promoter (C) preferably has a pKa of 1 to 20, and more preferably a pKa of 5 to 20 in terms of catalytic activity. The pKa is a value at 25° C. When the pKa is not less than the lower limit described above, the reactivity can be further improved. When the pKa is not more than the upper limit described above, the reactivity can be further improved.

Thus, the coordination promoter (C) is preferably a substance which is solid at 25° C. and has a pKa of 1 to 20, and more preferably a substance which is solid at 25° C. and has a pKa of 5 to 20.

<Organic (D)>

When the composition I contains the organic substance (D), further improved toughness can be imparted to the composition I and a shaped product obtained therefrom, and the design freedom can be further enhanced.

The organic substance (D) may be any of a polymer (D1) having a constitutional unit having one metal coordination site capable of coordinating to the metal atom α, a monomer (D2) having one metal coordination site defined above, and an organic substance (D3) having no coordination site defined above.

Examples of the metal coordination site of the organic substance (D) include those listed above as the examples of the metal coordination sites of the organic substance (B).

With respect to the polymer (D1), specific examples of its structural unit having one metal coordination site include an acrylic acid unit and a methacrylic acid unit. Further, the polymer (D1) does not have a structural unit having two or more metal coordination sites.

The organic substance (D3) may be a polymer or a monomer as in the case of the organic substance (B). The structure of the main chain of the polymer s not particularly limited, and examples thereof include a polyether structure, a polyolefin structure, a polyester structure, a polythiol structure, and a polyamide structure. The main chain may have any one of these structures, or may have two or more of the structures.

Specific examples of the organic substance (D) include a polymer having polyacrylic acid in the main chain, a monocarboxylic acid such as acrylic acid, and an epoxy resin.

<Liquid Medium (E)>

The liquid medium (E) functions as a solvent or a dispersion medium, and enhances the shapability of the composition I. When the composition I contains the resin (F), the liquid medium (E) is held by the resin (F) to form a gel.

The liquid medium (E) is a liquid that typically volatilizes under a temperature condition of 50 to 200° C. and caused a volume decrease of the composition.

Examples of the liquid medium (E) include an organic solvent such as dimethylformamide, water, and the like. One of these liquid media (E) may be used alone, or two or more thereof may be used in combination.

<Resin (F)>

The resin (F) is a resin capable of holding the liquid medium (E). When the composition I contains the resin (F), the composition I can be gelled by the liquid medium (E). The gel composition I can be easily shaped by a method such as extrusion or the use of a coater.

Specific examples of the resin (F) include polyacrylic acid, polyacrylate, polyester, an isobutylene-isoprene copolymer (butyl rubber), and polystyrene. One of these resins (F) may be used alone, or two or more thereof may be used in combination.

The resin (F) is a polymer having no metal coordination site.

The molecular weight of the resin (F) can be appropriately selected in consideration of shapability and the like.

The molecular weight of the resin (F) is preferably 10,000 or more, more preferably 20,000 to 3,000,000, and even more preferably 50,000 to 300,000, from the viewpoint of shapability.

The molecular weight of the resin (F) is a weight average molecular weight measured by GPC (gel permeation chromatography).

<Other Component (G)>

The other component (G) is a component that falls outside the definitions of the substance (A), the organic substance (B), the coordination promoter (C), the organic substance (D), the liquid medium (E), and the resin (F).

Examples of the component (G) include a resin serving as an additive such as a plasticizer (excluding, however, the organic substance (B), the coordination promoter (C) and the resin (F)) (e.g., polyvinyl isobutyl ether, etc.), inorganic fillers and surface treatment agents. One of these components may be used alone, or two or more of them may be used in combination.

One preferred embodiment of the composition I is a composition including a zinc compound as the substance (A), an organic substance having an aromatic ring having two or more carboxy groups as the organic substance (B) (for example, terephthalic acid, a polyether having a structural unit represented by the formula (b1)), and dicyandiamide as the coordination promoter (C). Such a composition can produce crystals upon heating.

Another preferred embodiment of the composition I is a composition including a zinc compound as the substance (A), an organic substance having an aromatic ring having two or more carboxy groups as the organic substance (B), and a ketoprofenamine salt as the coordination promoter (C). Such a composition can produce crystals upon light irradiation.

Still another preferred embodiment of the composition I is a composition including a zinc compound as the substance (A), an organic substance having an aromatic ring having two or more carboxy groups as the organic substance (B), and one or both of calcium oxide and iron as the coordination promoter (C). Such a composition can produce crystals with oxygen or moisture.

<Amount of Each Component>

In the composition I, the amount of the substance (A) is preferably from 20 to 80% by mass, and more preferably from 30 to 70% by mass, based on the total mass of the composition I. When the amount of the substance (A) is within the above range, the crystals can be obtained at a higher ratio.

In the composition I, the amount of the organic substance (B) is preferably from 10 to 50% by mass, and more preferably from 30 to 50% by mass, based on the total mass of the composition I. When the amount of the organic substance (B) is within the above range, the crystals can be obtained at a higher ratio.

In the composition I, the amount of the coordination promoter (C) is preferably 0.1 to 50% by mass, and more preferably 1 to 33% by mass, based on the total mass of the composition I. When the amount of the coordination promoter (C) is not less than the lower limit described above, the effect of promoting the coordination of the metal coordination sites β to the metal atom α is sufficiently exhibited, and when the amount is not more than the upper limit described above, the crystal ratio with respect to the total amount can be increased, and the function of the shaped product further improves.

In the composition I, the amount of the organic substance (D) is preferably 0% by mass or more and less than 50% by mass, and more preferably 0 to 10% by mass, based on the total mass of the composition I. When the amount of the organic substance (D) is not more than the upper limit described above, the excellent shapability is further enhanced.

In the composition I, the amount of the liquid medium (E) is preferably from 0 to 99% by mass, and more preferably from 0 to 1% by mass, based on the total mass of the composition I. When the amount of the liquid medium (E) is not more than the upper limit described above, further improved safety is secured. When the amount of the liquid medium (E) is more than 0% by mass, further improved shapability of the composition I is achieved.

For shaping the composition I by coating, the viscosity of the composition I is preferably low. Therefore, in this instance, the amount of the liquid medium (E) is preferably from 10 to 99% by mass, and more preferably from 30 to 85% by mass, based on the total mass of the composition I.

When the composition I is subjected to extrusion molding or injection molding, the amount of the liquid medium (E) is preferably from 5 to 80% by mass, and more preferably from 10 to 65% by mass, based on the total mass of the composition I. After the aforementioned shaping by coating or injection molding, the liquid solvent (E) may be dried off. The drying temperature and time are not particularly limited. The liquid solvent (E) remaining in the composition I (shaped product) after drying is preferably 0 to 10% by mass, and more preferably 0.1 to 3% by mass, based on the total mass of the composition I. If a small amount of the liquid solvent (E) remains in the composition I (shaped product), chipping of the cut surface may be suppressed while cutting or the like is implemented.

In the composition I, the amount of the resin (F) is preferably from 0 to 50% by mass, and more preferably from 0 to 30% by mass, based on the total mass of the composition I. When the amount of the resin (F) is not more than the upper limit described above, the ratio of the crystals after application of the stimulus is increased, and the exert function of the shaped product is further enhanced. When the amount of the resin (F) is more than 0% by mass, the effect of gelling the composition I is sufficiently exhibited.

In the composition the amount of the other component (G) is preferably from 0 to 10% by mass, and more preferably from 0 to 1% by mass, based on the total mass of the composition I. When the amount of the other component (G) is not more than the upper limit described above, the ratio of the crystals after application of the stimulus is increased, and the exert function of the shaped product further enhanced.

In the composition I, a part of the metal coordination sites of the organic substance (B) may be coordination-bonded to a part of the metal atoms α of the substance (A) to form crystals (MOF).

In the composition the amount of the crystals in which the metal coordination sites β are coordinated to the metal atom α is preferably 99% by mass or less, more preferably 50% by mass or less, more preferably 10% by mass or less, and particularly preferably 1% by mass or less, based on the total mass of the composition I. When the amount of the crystals is not more than the upper limit described above, excellent shapability is achieved.

The lower limit of the amount of the crystals in the composition I is not particularly limited, and may be 0% by mass.

The amount of the crystals can be measured by XRD (X-ray diffraction method).

The amount of the crystals can be adjusted by changing the ratio of the raw materials of the composition (I) and the intensity of the stimulus.

The method for producing the composition I is not particularly limited. For example, the composition I can be produced by a method in the substance (A), the organic substance (B), the coordination promoter (C), and if necessary, any one or more of the organic substance (D), the liquid medium (E), the resin (F), and other components (G) are mixed. As a mixing means for mixing the components, for example, kneading by a mixer and the like can be listed as an example. When the liquid medium (E) is not used, the components in the form of granules (powder) may be uniformly mixed by a known method. The order of mixing the components is not particularly limited.

The mixing of the coordination promoter (C) is to be implemented under such conditions as not to allow the coordination promoter (C) to undergo a reaction or a phase transition. All of the components may be mixed at once under such conditions as not to allow the coordination promoter (C) to undergo a reaction or a phase transition. Alternatively, the mixing may be implemented by a method in which a part or all of the components other than the coordination accelerator (C) are mixed, and the obtained mixture is mixed with the coordination promoter (C) and, if necessary, the remaining components under such conditions as not to allow the coordination promoter (C) to undergo a reaction or a phase transition. Another example is a method in which a mixture of the components other than the coordination accelerator (C) is prepared in advance, and only the coordination promoter (C) is added to the mixture the other components immediately before producing the shaped product (Y) described later.

The mixing conditions that do not allow the coordination promoter (C) to undergo a reaction or a phase transition can be appropriately determined, depending on the type of the coordination promoter (C).

For example, when heat causes the coordination promoter (C) to undergo a reaction or a phase transition, the mixing may be implemented under an environment with a temperature lower than the temperature at which the reaction or phase transition occurs. The temperature for such an environment may be, for example, a temperature which is 50° C. or more lower than the temperature at which the coordination accelerator (C) undergoes a reaction or a phase transition.

When light causes the coordination promoter (C) to undergo a reaction or a phase transition, the mixing may be implemented in a light-shielded environment.

When water causes the coordination promoter (C) to undergo a reaction or a phase transition, the mixing may be implemented in a low humidity environment, for example, in an environment with a relative humidity of 5% RH or less.

When oxygen causes the coordination promoter (C) to undergo a reaction or a phase transition, the mixing may be implemented in a low oxygen or oxygen-free environment, for example, in an atmosphere of an inert gas such as a nitrogen gas or an argon gas.

Since the composition I described above contains the substance (A), the organic substance (B) and the coordination promoter (C), MOF can be generated even without a high-pressure environment such as required in the solvothermal method, and the composition can be stored as a shapable material.

The metal coordination sites β of the organic substance (B) are unlikely to be coordinated to the metal atom α of the substance (A) unless the environment is a high-pressure environment, in a sealed space as used in the MOF synthesis by the solvothermal method. The coordination promoter (C) does not promote the coordination of the metal coordination sites β to the metal atom α before the reaction or phase transition is induced by stimulation.

While the coordination promoter (C) has not undergone a reaction or a phase transition, the coordination of the metal coordination sites β to the metal atom α and the generation of the crystal (MOF) accompanying the coordination do not proceed or proceed only slightly. Therefore, by placing the composition I in an environment that does now allow the coordination promoter (C) to undergo a reaction or a phase transition, the composition lean be stored without generating crystals.

Further, with the shaping conditions for shaping the composition I that do not allow the coordination promoter (C) to undergo a reaction or a phase transition, the composition I can be shaped without generating crystals.

After the shaping, when a stimulus is given to the obtained shaped product to allow the coordination promoter (C) to undergo a reaction or a phase transition, the coordination of the metal coordination sites β to the metal atom α proceeds in the shaped product even without a high-pressure environment in a sealed space, thereby forming crystals. For example, when the reaction of the coordination promoter (C) generates a substance acting as a catalyst promoting the coordination of the metal coordination sites β to the metal atom α, the action of the substance allows the metal coordination sites β to be coordinated to the metal atom α. When the coordination promoter (C) undergoes a phase transition from a solid to a liquid, the degree of freedom of movement of the components in the shaped article increases, and the coordination of the metal coordination sites β to the metal atom α proceeds, thereby generating the crystals.

Crystals can also be formed by giving a stimulus during the shaping.

By adjusting the stimulus to be given, the amount of the coordination promoter (C) that undergoes a reaction or a phase transition can be adjusted, and hence the rate of crystal formation can also be adjusted.

In this manner, a shaped product containing the crystals can be obtained. Since the crystals are formed after or during the shaping, it is possible to suppress the breakage of crystals by a load applied to the crystals during the shaping. Therefore, the functions of the crystals in the shaped product can be sufficiently exerted.

[Method for Producing Shaped Product]

The second aspect of the present invention relates to a method for producing a shaped product, comprising:

shaping the composition I to obtain a shaped product (Y) (hereinafter also referred to as "shaping process"); and applying a stimulus to the shaped product (Y) to form crystals in which the metal coordination sites β of the organic substance (B) are coordinated to the metal atom α of the substance (A) to thereby obtain a shaped product (Z) containing the crystals (hereinafter also referred to as "crystallization process").

The stimulus given to the shaped product (Y) allows the coordination promoter (C) to undergo a reaction ore a phase transition, and the coordination of the metal coordination sites β of the organic substance (B) to the metal atom α of the substance (A) proceeds to form crystals. Thus, the shaped product (Y) is turned into the shaped product (Z) containing crystals.

The shapes of the shaped product (Y) and the shaped product (Z) are not particularly limited. For example, each of these may in the form of a film, a porous structure, a honeycomb structure, or the like.

The method for shaping the composition I is not particularly limited, and a known shaping method can be employed. For example, when the composition I is solid, a method such as press molding, extrusion molding, or injection molding can be employed. When the composition I is in the form of liquid or gel, a method such as extrusion molding or die coating can be employed.

An uneven structure may be formed in advance on the surface of the mold used for molding so that a molded article having the uneven structure on the surface may be obtained.

Examples of the uneven structure include a shape in which a plurality of protrusions or dents are dispersedly positioned, a shape in which a plurality of ridges or grooves are positioned in parallel (so-called "line and space"), and an undulating shape. Examples of the shape of the protrusions or the dents include a columnar shape, a polygonal column shape, a hemispherical shape, a conical shape, and a polygonal pyramid shape.

The uneven structure on the surface of the molded body confers the following two effects.

One the two effects is an increase in the surface area. As for the crystals (MOF) in the shaped product, those located on the surface of the shaped product are more likely to exert their functions. The functions of the crystals mainly stem from the porousness thereof. As the surface area increases, the number of crystals located on the surface increases, and the crystals in the shaped product can be utilized more effectively.

Another one of the two effects is that a turbulent flow of gas, liquid, etc. is generated on the surface of the shaped product. The functions of the crystals include adsorption, storage and separation of gas and liquid, and the like. When gas or liquid to be subjected to adsorption, storage, separation, etc. passes over the surface of the shaped product, a flat surface of the shaped product allows the gas or liquid to flow undisturbed, which may be likely to reduce the concentration of the gas or liquid near the surface of the shaped product. On the other hand, an uneven structure on the surface generates a turbulent flow of the gas or liquid, so that the gas or liquid near the surface is stirred. Thus, the concentration of the gas or liquid to be subjected to adsorption, storage, separation, or the like on the surface of the shaped product does not decrease, so that the desired functions can be effectively exerted.

For increasing the surface area, it is preferable that the uneven structure has such a shape as would realize a surface area that is 1.1 times or more that of a plane having the same size in a top view.

On the other hand, when the surface area is extremely large with respect to the plane, the uneven structure is easily broken. A specific upper limit varies depending on the physical properties of the resin. However, for example, when a line and space having a large aspect ratio in the height direction (height/width) is formed on the surface such that the surface area is more than 10 times that of the plane, the even structure tends to become unstable and fragile.

Therefore, the surface area of the uneven structure is preferably not more than 10 times the surface area of a plane having the same size in a top view.

More specifically, the surface area of the uneven structure is preferably 1.1 to 10 times, and more preferably 1.2 to 3 times, the surface area of a plane having the same size in a top view.

The uneven structure effective for obtaining the desired functions can be determined by simulation based on the direction and speed of the flow of the target gas or liquid, and is preferably a shape in which a plurality of protrusions are dispersedly positioned, a line and space formed along a flow direction, or the like.

The uneven structure preferably includes a regular periodic structure in that the flow of gas or liquid can be easily spread over the entire surface of the shaped product. The regular periodic structure is also preferable from the viewpoint of easy production.

In the regular periodic structure, a plurality of structures (projections, dents, ridges, grooves, etc.) of the same size are arranged at a predetermined pitch in a predetermined direction on the surface of the shaped product. The plurality of structures may be oriented in one direction or two or more directions.

The size of the plurality of structures constituting the regular periodic structure is selected depending on the target gas or liquid. From the viewpoint of shapability, it is appropriate that the width relative to the orientation direction (diameter of the projection or the dent, the width of the ridge or the groove, etc.) is in the range of 20 nm to 1 mm. The aspect ratio in the height direction is preferably 10 or less from the viewpoint of durability. The pitch may be, for example, 20 nm to 5 mm.

The shaping process may be performed under an atmospheric pressure environment, or may be performed under a pressurized environment.

The pressure for performing the shaping process s preferably 1 to 10,000 atm, more preferably 1 to 100 atm. When the pressure is not more than the upper limit described above, there is no need to use a sealed container unlike the case of the solvothermal 1 method, and the productivity of the shaped product (Z) is excellent.

The shaping process is preferably performed under the condition such that the amount of the crystals in the obtained shaped product (Y) is 99% by mass or less, based on the total mass of the shaped product (Y). The amount of the crystals in the shaped product (Y) is more preferably 50% by mass or less, even more preferably 10% by mass or less, and particularly preferably 1% by mass or less. When the amount of the crystals in the shaped product (Y) is not more than the upper limit described above, excellent shapability is achieved.

The lower limit of the amount of the crystals in the shaped product (Y) is not particularly limited, and may be 0% by mass.

The difference in the amount of the crystals between the shaped product (Y) and the composition I before shaping is preferably 10% by mass or less, more preferably 1% by mass or less.

For adjusting the difference so as not to exceed the upper limit described above, the shaping process is preferably implemented under such conditions as not to allow the coordination promoter (C) to undergo a reaction or a phase transition. The conditions that do not allow the coordination promoter (C) to undergo a reaction or a phase transition are as described above.

The stimulus to be given the shaped product (Y) during the crystallization process is a stimulus for allowing the coordination promoter (C) to undergo a reaction or a phase transition, and is preferably at least one selected from the group consisting of heat, light, water and oxygen. The stimulus for causing the coordination promoter (C) to undergo a reaction or a phase transition may be of one type or two or more types.

As for the heat, the temperature thereof may be, for example, 40 to 500° C. Examples of the light include ultraviolet light, visible light, and infrared light. The irradiation amount of light can be appropriately selected depending on the type of light, the type of the coordination promoter (C), etc., and may be, for example, not less than 1 mJ/cm$^2$ of ultraviolet light having a wavelength of 360 nm. Examples of the method for combining two or more different stimuli include a method of contacting with hot water, a method of exposing to steam, and a method of heating or irradiating light in an atmosphere containing oxygen.

The crystallization process may be performed under an atmospheric pressure environment, or may be performed under a pressurized environment.

The pressure for performing the crystallization process is preferably 1 to 10,000 atm, and more preferably 1 to 100 atm. When the pressure is not more than the upper limit described above, there is no need to use a sealed container unlike the case of the solvothermal method, and the productivity of the shaped product (Z) is excellent.

In the crystallization process, the amount of the crystals in the shaped product (Z) is preferably adjusted to 0.1% by mass or more. The amount of the crystals in the shaped product (Z) is more preferably 1% by mass or more, even more preferably 10% by mass or more, and particularly preferably 30% by mass or more. When the amount of the crystals in the shaped product (Z) is not less than the lower limit described above, the shaped product (Z) exhibits excellent functionality as a porous body.

The upper limit of the amount of the crystals in the shaped article (Z) is not particularly limited, and may be, for example, 50% by mass.

That is, the amount of the crystals in the shaped product (Z) is preferably 0.1% by mass to 50% by mass. The amount of the crystals in the shaped product (7) is more preferably 1% by mass to 50% by mass, even more preferably 10% by mass to 50% by mass, and particularly preferably 30% by mass to 50% by mass.

The difference in the amount of the crystals between the shaped product (Z) and the shaped product (Y) is preferably 1% by mass or more, and more preferably 10% by mass or more.

After the crystallization process, if necessary, the Obtained shaped product (Z) may be subjected to a treatment such as washing with a liquid, surface treatment with a coating agent, a surface physical treatment for exposing the buried crystals, or a surface shaping treatment for forming uneven structure on the surface of the shaped product.

When the composition I contains a resin component (i.e., the organic substance (B) which is a polymer, the resin (F), etc.), a part of the crystals (MOF) are buried in the resin in the shaped product (Z) obtained in the crystallization process. By subjecting the shaped product (Z) to a surface physical treatment to remove the resin coating forming the surface layer, the buried crystals can be exposed on the surface, and the crystals are allowed to fully exert their functions (adsorption function and the like, which are hereinafter also referred to as "MOF functions") stemming from the porousness of the crystals. For example, the gas adsorption function greatly improves.

The surface physical treatment is not particularly limited as long as it does not damage the shaped product, and a known method can be employed.

All that is needed to have the crystals exposed is to remove the resin thin film present on the crystals, and therefore a relatively mild surface physical treatment is preferable. Examples of such a surface physical treatment include a corona treatment, a plasma treatment, and a flame treatment. These treatments can be suitably implemented for only activating the surface without causing severe damage to the shaped product.

However, the surface physical treatment is not limited to these examples, and other methods suited for purpose can also be employed, such as a physical surface roughening method (e.g., sandblasting), a method of applying a strong electric stress (e.g., are discharge), or the like.

The specific treatment conditions are preferably determined while actually performing the treatment of the shaped product and checking the results.

The shaped product obtained by the method of the present embodiment preferably has a ratio of MOF exposed on the surface (hereinafter, also referred to as "exposed MOF ratio") of 5 to 98%.

The exposed MOF ratio is an index representing; ratio of surface section occupied by the MOF (crystals) exposed on the surface of the shaped product in the surface area of the shaped product, and is obtained by the following equation (1). When the exposed MOF ratio is not less than the lower limit described above, further improved MOF functions are achieved. When the exposed MOF ratio is not more than the upper limit described above, breakage or release of the MOF is suppressed, and the MOF functions can be persistently exhibited.

The exposed MOF ratio is more preferably from 10 to 90% even more preferably from 15 to 80%, and particularly preferably from 46 to 80%.

$$\text{Exposed MOF ratio}=(A/B)\times 100 \quad (1)$$

wherein:
 A represents the amount (atm %) of metal atoms attributable to MOF on the surface of the shaped product measured by X-ray photoelectron spectroscopy (hereinafter also referred to as "XPS"), and
 B represents the total amount of metal atoms (atm %) present in MOF.

The amount A of the metal atoms is a ratio of the atomic weight of atoms which are not smaller in atomic weight than lithium with respect to the total atomic weight (100 atm %) in the measurement by XPS. The details of the method for measuring the amount A of the metal atoms are shown in the Examples section described later.

The amount B of the metal atoms in the MOF is a ratio of the atomic weight of atoms constituting the MOF which are not smaller in atomic weight than lithium with respect to the total atomic weight (100 atm %). The amount B of the metal atoms is calculated from the MOF composition formula.

When the shaped product includes a plurality of MOFs, the value of B is a weighted average of the respective amounts of the MOFs obtained using the mass of each MOF as a weight.

The exposed MOF ratio can be adjusted by changing the amount of the crystals in the shaped product, the conditions of the surface physical treatment applied to the shaped product, and the like.

The exposed MOF ratio can be easily confirmed by performing elemental analysis on the surface of the shaped product using an energy dispersive X-ray analysis (EDX) device attached to a scanning electron microscope (SEM). The value according to EDX does not always match the value according to the above equation (1), but shows a similar tendency to the value according to the above equation (1). For example, the larger the value by EDX, the larger the value by the above equation (1) tends to be.

Hereinbelow, a specific example of the method for measuring the exposed MOF ratio is shown.

Using an XPS apparatus (manufactured by Kratos), the measurement is implemented under conditions described below with respect to a measurement sample obtained by cutting a piece of 10 mm×10 mm×5 mm or less (thickness) from an approximately central portion of the shaped product (laminated body or sheet) the cut surface of the shaped product, a section of 1×2 mm near the center is used as a measurement target surface, and the amount A (atm %) of metal atom (Zn or Zr) on the measurement target surface is measured. From this value and the amount B (atm %) of the metal atom (Zn or Zr) of the MOF used for the shaped product, the exposed MOF ratio (%) is calculated by the above equation (1).

XPS measurement conditions: A wide spectrum and a narrow spectrum of a target element are measured using an X-ray source AlKα (monochrome), and atm % is calculated from these results.

The uneven structure formed on the surface of the shaped product by the surface shaping treatment is as described above.

The surface shaping method, that is, the method for forming the uneven structure is not particularly limited, and a general method can be used. Examples of the method include a method in which a mold having an uneven structure on its surface is pressed against the surface of the shaped product while heating to transfer the uneven structure onto the surface of the shaped product, a method in which the surface of the shaped product is subjected to laser cutting, and the like.

For forming a fine uneven structure having a pitch of less than 1 μm, it is preferable to use a nanoimprint technique. The nanoimprint technique can be broadly classified into a thermal nanoimprint technique that presses a heated mold against a target surface, an optical nanoimprint technique in which a photocurable resin material is cast into a transparent mold and solidified, and a microcontact printing technique that attaches a target shaped product to a relief plate good mold release, such as one made of silicone, and prints the relief pattern on the desired portions of the shaped product.

Examples of the photocurable resin material include a composition containing a polymerizable component such as a monomer and an oligomer, and a photopolymerization initiator. The polymerizable component may be the organic substance (B). Examples of the organic substance (B) as the polymerizable component include an organic substance having the metal coordination site β and a functional group that causes a curing reaction by the photopolymerization initiator. Examples of the functional group that causes a curing reaction by the photopolymerization initiator include radically polymerizable unsaturated bonds. As specific examples of the suitable compounds, (meth)acrylates and styrene compounds can be listed. Especially, for curing, a polyfunctional (meth)acrylate, a divinylbenzene compound and the like, which are compounds having a plurality of polymerizable functional groups, can be listed.

The third aspect of the present invention relates a method for producing a shaped product, which include a process where the stimulus is applied to the composition I while shaping the composition I, so as to form the crystals in which the metal coordination sites β of the organic substance (B) are coordinated to the metal atom α of the substance (A) to thereby obtain the shaped product (Z) containing the crystals (hereinafter also referred to as "shaping/crystallization process").

The stimulus given to the composition I during the shaping of the composition I allows the coordination promoter (C) to undergo a reaction ore a phase transition, and the coordination of the metal coordination sites β of the organic substance (B) to the metal atom α of the substance (A) proceeds to form a crystal. Thus, the shaped product (Z) containing a crystal is obtained.

As a method for shaping the composition I, a known shaping method can be employed as in the case described above.

The stimulus to be given to the composition I is a stimulus for allowing the coordination promoter (C) to undergo a reaction or a phase transition as in the case described above, and is preferably at least one selected from the group consisting of heat, light, water and oxygen.

The shaping/crystallization process may be performed under an atmospheric pressure environment, or may be performed under a pressurized environment.

The pressure for performing the shaping/crystallization process is preferably 1 to 10,000 atm, and more preferably 1 to 10 atm. When the pressure is not more than the upper limit described above, there is no need to use a sealed container unlike the case of the solvothermal method, and the productivity of the shaped product (Z) is excellent.

In the shaping/crystallization process, the amount of the crystals in the shaped product (Z) is preferably adjusted to 0.1% by mass or more. The more preferable amounts of the crystals in the shaped product (Z) is the same as described above.

The difference in the amount of the crystals between the shaped product (Z) and the composition I before shaping is preferably 1% by mass or more, more preferably 10% by mass or more.

After the shaping/crystallization process, if necessary, the obtained shaped product (Z) may be subjected to a treatment such as washing with a liquid, surface treatment with a coating agent, a surface physical treatment for exposing the buried crystals, or a surface shaping treatment for forming uneven structure on the surface of the shaped product.

The shaped product (Z) obtained by the method according to the second or third aspect contains crystals, i.e., MOF, in which the metal coordination sites β of the organic substance (B) are coordinated to the metal atom α of the substance (A).

The shaped product (Z) may or may not contain the coordination promoter (C). When the washing process is implemented, a shaped product (Z) containing the coordination promoter (C) in a reduced amount or containing no coordination promoter (C) is obtained.

(Shaped Product)

The fourth aspect of the present invention relates to a shaped product including: a crystal in which the metal coordination sites of the organic substance (B) are coordinated to the metal atom of the substance (A); and the coordination promoter (C).

The shaped product of this aspect can be obtained by the method for producing a shaped product according to the second or third aspect described above.

The adsorption performance of the shaped product can be evaluated using the BET specific surface area as an index. The BET specific surface area is a specific surface area measured by a BET method using nitrogen as an adsorption gas. The measurement can be performed using a BET specific surface area meter (manufactured by Shimadzu Corporation).

The use of the obtained shaped product can be expanded to various applications, the specific examples of which include gas separation, gas storage, sensors, DDS (drug delivery system), electromagnetic wave shield, selective catalysts, dielectric, detection systems using a precursor of porous simple metal, detection systems using a precursor of porous metal oxide, capacitors, electrodes, and the like.

Other Embodiments

The present invention is not limited to the embodiments described above in relation to the first to fourth aspects, and various alterations such as addition, omission and substitution of any components, etc. may be made as long as such alterations do not deviate from the gist of the present invention.

An example of another embodiment of the present invention is a composition (hereinafter also referred to as "composition II") including:

a substance (A2) including at least one metal atom (hereinafter also referred to as "metal α2") selected from the group consisting of zinc, copper, cobalt, chromium, aluminum, niobium, zirconium, cadmium, nickel, vanadium, titanium, and molybdenum; and an organic substance (B2) having at least two stimulus-responsive metal coordination sites β3 in which metal coordination sites (hereinafter also referred to as "metal coordination sites β2") capable of being coordinated to the metal atom α2 are protected by the protective groups that can be released when a stimulus is applied.

The substance (A2) may be the same as the substance (A) except that the atom α is the metal atom α2.

The organic substance (B2) may be the same as the organic substance (except that the metal coordination sites β are the metal coordination sites β2 and the metal coordination sites β2 are protected by the protective groups.

Since the composition II contains the substance (A2) and the organic substance (B2), MOF can be generated even without a high-pressure environment such as required in the solvothermal method, and the composition II can be stored as a shapable material.

The metal coordination sites β2 of the organic substance (B2) are readily coordinated to the metal atom α2 of the substance (A2). Therefore, when the metal coordination sites β2 are not protected by the protective groups, the generation of MOF proceeds rapidly even without a high-pressure environment such as required in the solvothermal method, and the resulting cannot be stored as a shapable material.

The stimulus-responsive metal coordination sites β3 formed by protecting the metal coordination sites β2 with the protective groups are not or are unlikely to be coordinated to the metal atom α2 even in a high-pressure environment in a sealed space as used in the synthesis of MOF by the solvothermal method.

Therefore, in the composition II before receiving the stimulus, the coordination of the metal coordination sites β3 to the metal atom α2 and the generation of the crystal (MOF) accompanying the coordination do not proceed or proceed only slightly. For this reason, by placing the composition II in an environment that does not allow the protective groups of the stimulus-responsive metal coordinating sites β3 to be released, the composition II can be stored without generating crystals.

In addition, when the shaping conditions for shaping the composition II are adjusted so as not to allow the protective groups to be released, the composition II can be shaped without generating crystals.

After the shaping, when a stimulus is given to the obtained shaped product to release the protective groups of the stimulus-responsive metal coordination sites β3 and to form the metal coordination sites β2, the coordination of the metal coordination sites β2 to the metal atom α2 proceeds in the shaped product even without a high-pressure environment in a sealed space, thereby forming crystals.

Crystals can also be formed by giving a stimulus during the shaping.

By adjusting the stimulus to be given, the amount of the protecting groups to be released can be adjusted, and hence the rate of crystal formation can be adjusted as well.

In this manner, a shaped product containing the crystals can be obtained. Since the crystals are formed after or during the shaping, it is possible to suppress the breakage of crystals by a load applied to the crystals during the shaping. Therefore, the functions of the crystals in the shaped product can be sufficiently exerted.

The protective groups are not particularly limited as long as such protective groups can be released by an intended stimulus. For example, when the metal coordination sites β2 of the organic substance (B2) are carboxy groups, a known protective group such as a benzyl group, an allyl group, and a diphenylmethyl group can be adopted. In addition, the method for introducing the protective groups and the method for releasing the protective groups can be performed by known methods.

For example, a method in which a carboxy group is protected by esterification with a photolabile protective group and deprotected by light irradiation (see WO2009/113322) can be employed.

The composition II may further contain at least one component selected from the group consisting of the above-mentioned coordination promoter (C), organic substance (D), liquid medium (E), resin (F), and other components (G). The amounts of these components may be the same as in the case of the composition I.

The production of a shaped product using the composition II can be carried out following the same procedure as in the production of a shaped product using the composition I. For example, by using the composition II instead of the composition I in the production method of the second or third aspect, a shaped product (Z2) containing crystals can be obtained.

EXAMPLES

Hereinbelow, the present invention will be described in more detail with reference to the Examples which, however, should not be construed as limiting the present invention. The compounds, solvents and the like used in Examples and Comparative Examples were all commercial products. The "room temperature" means a temperature within the range of 15±15° C.

(Evaluation of Crystal Formation)

The presence or absence of crystals formed in the shaped products was visually checked.

Example 1

0.34 g of terephthalic acid was dissolved in 40 g of dimethylformamide, followed by addition of 1.21 g of zinc nitrate. The resulting mixture was stirred until the added compounds were completely dissolved to thereby obtain a solution. Next, 1 g of an epoxy resin was added to the solution, and the resulting mixture was vigorously stirred for 5 minutes. Then, 2.0 g of dicyandiamide was added and the resulting was stirred for 5 minutes to thereby obtain a solution composition. The preparation of the above composition was implemented at room temperature. As the epoxy resin, a phenoxy resin (grade 1256) manufactured by Mitsubishi Chemical Corporation was used.

The obtained composition was applied to a thickness of 100 μm with a coater and dried by heating at 80° C. for 5 minutes to obtain a flexible film (shaped product). No microcrystals were found in the resulting film. No dimethylformamide remained in the dried film under the above drying conditions.

When the obtained film was heated at 180° C. for 30 minutes, a film (a shaped product after stimulation) with visible white microcrystals was obtained.

Example 2

A solution composition was prepared and a flexible film (shaped product) was produced from the solution composition following the same procedure as in Example 1 except that terephthalic acid was replaced by a polyether of terephthalic acid (weight average molecular weight: 1,000) (a polyether having a structural unit represented by the formula (b1)). No microcrystals were found in the resulting film.

When the obtained film was heated at 180° C. for 30 minutes film it visible white microcrystals was obtained.

Comparative Example 1

A solution composition was prepared and a flexible film (shaped product) was produced from the solution composition following the same procedure as in Example 1 except that dicyandiamide was not added after the epoxy resin was added to the solution and stirred. No microcrystals were found in the resulting film.

The obtained film was heated at 180° C. for 30 minutes. No microcrystals were found in the resulting film.

Comparative Example 2

In Comparative Example 1, an epoxy resin was added to the solution, followed by stirring. Then, 2.5 g of triethylamine was added thereto and the resulting was stirred for 5 minutes to obtain a solution composition. White microcrystals were found in this composition.

The obtained composition was applied a thickness of 100 μm with a coater and dried by heating at 80° C. for 5 minutes to obtain a flexible film (shaped product). White microcrystals were found in this film. Further, this film had a non-uniform distribution of crystals in the film. This is considered to be because the crystallization progressed in the solution state, so that the crystals could not be sufficiently dispersed in the composition, and the crystals aggregated during the drying step.

Comparative Example 3

A solution composition was prepared and a flexible film (shaped product) was produced from the solution composition following the same procedure as in Example 1 except that 0.33 g of diphenyl was used instead of terephthalic acid.

This film was substantially the same as that in Example 1, and no microcrystal was observed.

When the obtained film was heated at 180° C. for 30 minutes, there was no change in the film.

Comparative Example 4

A solution composition was prepared and a flexible film (shaped product) was produced from the solution composition following the same procedure as in Example 1 except that rhenium oxide (VII) was used instead of zinc nitrate. This film was the same as that in Example 1, and no microcrystal was observed.

When the obtained film was heated at 180° C. for 30 minutes, there was no change in the film.

Example 3

A solution composition was prepared and a flexible film (shaped product) was produced from the solution composition following the same procedure as in Example 1 except that the drying conditions were changed and the amount of dimethylformamide remaining in the film after drying was set to 10% based on the total mass of the film. This film was a flexible film almost similar to that of Example 1, and no microcrystal was observed.

When the obtained film was heated at 180° C. for 30 minutes, film with visible white microcrystals vas obtained.

Example 4

A solution composition was prepared and a flexible film (shaped product) was produced from the solution composition following the same procedure as in Example 3 except that 0.2 g of polyacrylic acid was added before drying the solvent. This film was a flexible film almost similar to that of Example 3 and no al was observed.

When the obtained film was heated at 180° C. for 30 minutes, a film with visible white microcrystals was obtained.

Example 5

A solution composition was prepared and a flexible film (shaped product) was produced from the solution composition following the same procedure as in Example 1 except that ketoprofen triethylamine salt was added instead of dicyandiamide. This film was a flexible film almost similar to that of Example 1, and no microcrystal was observed.

When the obtained film was irradiated with ultraviolet rays (mercury lamp, 20 J/cm$^2$), a film with visible white microcrystals was obtained.

Example 6

A solution composition was prepared and a flexible film (shaped product) was produced from the solution composition following the same procedure as in Example 1 except that 1 g of calcium oxide and 1.25 g of pyridine were added instead of dicyandiamide. After the formation of the film, the obtained film was sandwiched between release films. This film was a flexible film almost similar to that of Example 1, and no microcrystal was observed.

The release films were peeled off from the obtained film and the film was allowed to stand at room temperature for 1 day. As a result, a film with visible white microcrystals was obtained.

Example 7

A solution composition was prepared and a flexible film (shaped product) was produced from the solution composition following the same procedure as in Example 6 except that 1 g of iron powder and 1.25 g of pyridine were added instead of calcium oxide and pyridine. This film was a flexible film almost similar to that of Example 6, and no microcrystal was observed.

The release films were peeled off from the obtained film and the film was allowed to stand at room temperature for 1 day. As a result, a film with visible white microcrystals was obtained.

Table 1 shows the compositions and the presence or absence of crystals with respect to the films (shaped products) obtained in Examples 1 to 7 and Comparative Examples 1 to 4, and the presence or absence of crystals in the shaped products after stimulation.

TABLE 1

| | Composition | | | | | | Presence of absence of crystals | |
| --- | --- | --- | --- | --- | --- | --- | --- | --- |
| | Organic substance (B) | Substance (A) | Coordination promoter (C) | Organic substance (D) | Liquid medium (E) | Resin (F) | Shaped product | Stimulated shaped product |
| Ex. 1 | Terephthalic acid | Zinc nitrate | Dicyandiamide | Epoxy resin | — | — | No | Yes |
| Ex. 2 | Polyether of terephthalic acid | Ditto | Ditto | Ditto | — | — | No | Yes |
| Comp. Ex. 1 | Terephthalic acid | Ditto | — | Ditto | — | — | No | No |
| Comp. Ex. 2 | Terephthalic acid | Ditto | Triethylamine | Ditto | — | — | Yes | Yes |
| Comp. Ex. 3 | Diphenyl | Ditto | Dicyandiamide | Ditto | — | — | No | No |
| Comp. Ex. 4 | Terephthalic acid | Rhenium(VII) oxide | Dicyandiamide | Ditto | — | — | No | No |
| Ex. 3 | Terephthalic acid | Zinc nitrate | Dicyandiamide | Ditto | Dimethyl formamide (10%) | — | No | Yes |
| Ex. 4 | Terephthalic acid | Zinc nitrate | Dicyandiamide | Ditto | Dimethyl formamide (10%) | Polyacrylic acid | No | Yes |
| Ex. 5 | Terephthalic acid | Zinc nitrate | Ketoprofen triethylamine salt | Ditto | — | — | No | Yes |

TABLE 1-continued

| | Composition | | | | | | Presence of absence of crystals | |
|---|---|---|---|---|---|---|---|---|
| | Organic substance (B) | Substance (A) | Coordination promoter (C) | Organic substance (D) | Liquid medium (E) | Resin (F) | Shaped product | Stimulated shaped product |
| Ex. 6 | Terephthalic acid | Zinc nitrate | Calcium oxide/pyridine | Ditto | — | — | No | Yes |
| Ex. 7 | Terephthalic acid | Zinc nitrate | Iron powder/pyridine | Ditto | — | — | No | Yes |

Example 8

A metal roll having a line-and-space structure having a pitch of 20 μm and a depth of 10 μm on the surface thereof was pressed against the flexible film (shaped product) obtained in Example 1 to obtain a film having a shaped surface. A microscopic observation revealed that a line and space having a pitch of about 20 μm and a depth of about 10 μm was formed on the surface of the film.

The invention claimed is:

1. A composition comprising:
a substance (A) comprising at least one metal atom selected from the group consisting of zinc, cobalt, niobium, zirconium, cadmium, copper, nickel, chromium, vanadium, titanium, molybdenum, magnesium, iron and aluminum, with the proviso that a metal organic framework is excluded;
an organic substance (B) having at least two metal coordination sites capable of being coordinated to the metal atom to form a crystal of a metal organic framework, wherein the metal coordination sites are of at least one type selected from the group consisting of a carboxy group and a metal organic framework; and
a coordination promoter (C) that undergoes a reaction or a phase transition upon stimulation to promote the coordination of the metal coordination sites of the organic substance (B) to the metal atom of the substance (A),
wherein the coordination promoter (C) is at least one selected from the group consisting of dicyandiamide, a tertiary amine that is crystalline at room temperature, a combination of calcium oxide and pyridine, and a combination of iron and pyridine.

2. The composition according to claim 1, wherein the stimulation is at least one selected from the group consisting of heat, light, water, and oxygen.

3. The composition according to claim 1, wherein the coordination promoter (C) is solid at 25° C. and has a pKa of 1 to 20.

4. The composition according to claim 1, wherein a crystal in which the metal coordination sites of the organic substance (B) are coordinated to the metal atom of the substance (A) is present in an amount of 50% by mass or less.

5. The composition according to claim 1, wherein a crystal in which the metal coordination sites of the organic substance (B) are coordinated to the metal atom of the substance (A) is present in an amount of 10% by mass or less.

6. The composition according to claim 1, wherein a crystal in which the metal coordination sites of the organic substance (B) are coordinated to the metal atom of the substance (A) is present in an amount of 1% by mass or less.

7. The composition according to claim 1, wherein the organic substance (B) has an aromatic ring having one or more of the metal coordination sites.

8. The composition according to claim 1, wherein the organic substance (B) has an aromatic ring having two or more of the metal coordination sites.

9. The composition according to claim 8, wherein the metal coordination sites are carboxy groups.

10. The composition according to claim 1, wherein the organic substance (B) has a molecular weight of 100 or more.

11. The composition according to claim 1, wherein the organic substance (B) is a polymer having a main chain and a pendant structure bonded to the main chain, wherein the pendant structure comprises the metal coordination sites.

12. The composition according to claim 11, wherein the main chain comprises at least one structure selected from the group consisting of a polyether structure, a polyolefin structure, a polyester structure, a polythiol structure, and a polyamide structure.

13. The composition according to claim 1, wherein the substance (A) is at least one substance selected from the group consisting of a simple metal and a metal compound having a valence of 1 to 5.

14. The composition according to claim 1, which further comprises at least one organic substance (D) selected from the group consisting of a polymer having a constitutional unit having one metal coordination site capable of being coordinated to the metal atom to form a crystal, a monomer having one metal coordination site defined above, and an organic substance having no metal coordination site defined above.

15. The composition according to claim 1, which further comprises a liquid medium (E).

16. The composition according to claim 15, wherein the amount of the liquid medium (E) is 99% by mass or less.

17. The composition according to claim 15, which further comprises a resin (F) capable of holding the liquid medium (E).

18. A shaped product comprising:
a crystal of metal organic framework in which metal coordination sites of an organic substance (B) are coordinated to a metal atom of a substance (A), wherein the organic substance (B) has at least two metal coordination sites which are of at least one type selected from the group consisting of a carboxy group and a metal organic framework, and the substance (A) comprises at least one metal atom selected from the group consisting of zinc, cobalt, niobium, zirconium, cadmium, copper, nickel, chromium, vanadium, titanium, molybdenum, magnesium, iron and aluminum, with the proviso that an metal organic framework is excluded; and a coordination promoter (C) that undergoes a reaction or a phase transition upon stimulation to promote the coordination of the metal coordination sites of the organic substance (B) to the metal atom of the substance (A), wherein the coordination promoter (C) is at least one selected from the group consisting of dicyandiamide, a tertiary amine that is crystalline at room temperature, a combination of calcium oxide and pyridine, and a combination of iron and pyridine.

19. A method for producing a shaped product, comprising:

shaping the composition according to claim 1 to obtain a shaped product (Y); and applying a stimulus to the shaped product (Y) to form a crystal in which the metal coordination sites of the organic substance (B) are coordinated to the metal atom of the substance (A) to thereby obtain a shaped product (Z) containing the crystal.

20. The method according to claim 19, wherein the stimulus is at least one selected from the group consisting of heat, light, water, and oxygen.

21. The method according to claim 19, wherein the amount of the crystal in the shaped product (Y) is 99% by mass or less.

22. The method according to claim 19, wherein the shaped product (Z) is obtained such that the amount of the crystal in the shaped product (Z) is 0.1% by mass or more.

23. A method for producing a shaped product, comprising: applying a stimulus to the composition of claim 1 while shaping the composition, so as to form a crystal in which the metal coordination sites of the organic substance (B) are coordinated to the metal atom of the substance (A) to thereby obtain a shaped product (Z) containing the crystal.

* * * * *